US012635865B2

(12) United States Patent
Gordon

(10) Patent No.: US 12,635,865 B2
(45) Date of Patent: May 26, 2026

(54) SYSTEMS AND METHODS FOR ORIENTING TOOLS WITHIN FLEXIBLE ELONGATED DEVICES

(71) Applicant: Intuitive Surgical Operations, Inc., Sunnyvale, CA (US)

(72) Inventor: Lucas S. Gordon, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 320 days.

(21) Appl. No.: 18/243,783

(22) Filed: Sep. 8, 2023

(65) Prior Publication Data

US 2024/0081628 A1 Mar. 14, 2024

Related U.S. Application Data

(60) Provisional application No. 63/405,110, filed on Sep. 9, 2022.

(51) Int. Cl.
*A61B 1/00* (2006.01)
*A61B 1/018* (2006.01)

(52) U.S. Cl.
CPC .......... *A61B 1/018* (2013.01); *A61B 1/00137* (2013.01)

(58) Field of Classification Search
CPC ... A61B 1/018; A61B 1/00137; A61B 1/0034; A61B 1/00–32; A61B 1/0135; A61B 1/00154; A61B 1/00128; A61B 1/00147; A61B 8/4218; A61B 2017/0034; A61M 2025/0681

USPC .................. 600/104; 604/264, 523, 539, 538
See application file for complete search history.

(56) References Cited

U.S. PATENT DOCUMENTS

| | | | | | |
|---|---|---|---|---|---|
| 4,807,598 A | * | 2/1989 | Hasegawa | .......... | A61B 1/00071 600/153 |
| 2007/0038158 A1 | * | 2/2007 | Nita | ................ | A61B 17/22012 601/2 |
| 2016/0106404 A1 | * | 4/2016 | Melanson | .......... | A61B 17/2909 606/1 |
| 2017/0224194 A1 | * | 8/2017 | Fujitani | ................ | A61B 1/0052 |
| 2018/0280660 A1 | * | 10/2018 | Landey | .............. | A61B 1/00149 |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

*Primary Examiner* — Anh Tuan T Nguyen
*Assistant Examiner* — James Edward Boice
(74) *Attorney, Agent, or Firm* — Osha Bergman Watanabe & Burton LLP

(57) ABSTRACT

A medical instrument includes a tool having a mating tool portion with a first set of angled flats and a flexible elongated body having a mating channel portion with a second set of angled flats. When the tool is inserted into a channel of the flexible elongated body, the first set of angled flats engages with the second set of angled flats. The first and second sets of angled flats may be configured such that the tool is oriented into one of a plurality of predetermined orientations relative to the flexible elongated body when the first and second sets of angled flats are engaged during tool insertion.

18 Claims, 7 Drawing Sheets

SYSTEMS AND METHODS FOR ORIENTING TOOLS WITHIN FLEXIBLE ELONGATED DEVICES

CROSS-REFERENCE TO RELATED APPLICATIONS

This application claims the benefit of priority under 35 U.S.C. § 119(e) to U.S. Provisional Patent Application Ser. No. 63/405,110, filed on Sep. 9, 2022, which is hereby incorporated by reference herein in its entirety.

FIELD

The present disclosure is directed to systems and methods for orienting tools within flexible elongated devices.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, and/or therapeutic instruments) to reach a target tissue location. One such minimally invasive technique is to use a flexible and/or steerable elongated device, such as a flexible catheter that can be inserted into anatomic passageways and navigated toward a region of interest within the patient anatomy. Vision probes and other medical tools may be deployed through an interior channel of the catheter or other flexible elongated device to help navigate the catheter to and perform a medical procedure at the region of interest.

SUMMARY

In some embodiments, a medical system includes a tool including a mating tool portion with a first set of angled flats disposed around a cross sectional perimeter of the mating tool portion. The medical system also includes a flexible elongated body including a channel extending through the flexible elongated body, wherein the tool is configured to be inserted into the channel, and wherein the channel includes a mating channel portion with a second set of angled flats disposed around a cross sectional perimeter of the mating channel portion. The first set of angled flats of the mating tool portion and the second set of angled flats of the mating channel portion are angled relative to a longitudinal axis of the flexible elongated body when the tool is inserted in the channel, and the first set of angled flats of the mating tool portion is configured to be engaged with the second set of angled flats of the mating channel portion when the tool is inserted into the channel.

In some embodiments, a method for inserting a tool into a medical instrument includes advancing the tool through a channel extending through a flexible elongated body of the medical instrument. The method also includes engaging a first set of angled flats of a mating tool portion of the tool with a second set of angled flats of a mating channel portion of the channel to rotationally orient the tool within the channel. The first set of angled flats and the second set of angled flats are angled relative to a longitudinal axis of the channel when the tool is disposed in the channel.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
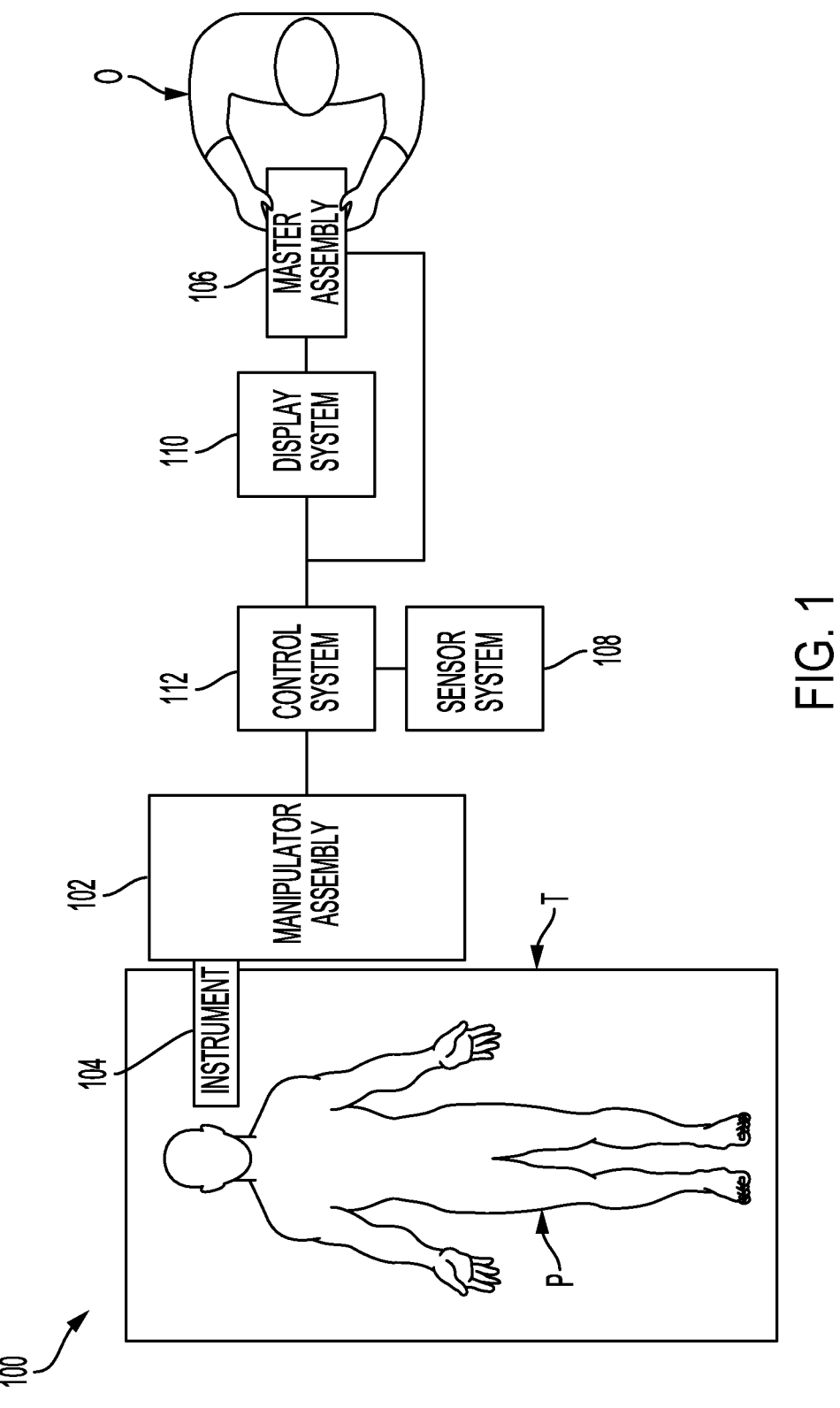
FIG. 1 is a schematic of an exemplary teleoperated medical system in accordance with some embodiments of the present disclosure.

In some medical procedures, an operator may navigate a flexible elongated device through a patient to a procedure site. The flexible elongated device may include a flexible elongated body, such as a catheter, and a medical tool disposed within a channel extending through the flexible elongated body. The rotational orientation of the medical tool relative to the flexible elongated body may need to be synchronized during navigation and the medical procedure.

To maintain the alignment of the medical tool within the flexible elongated body, a medical tool may include a mating key that matches a keyway formed in a channel of a flexible elongated body. For example, a flexible elongated body may have a working channel with a square cross-section along a portion of its length (a square keyway) and a tool may have a round shaft except for a square shaped portion (a square key) that mates with the square shaped working channel of the flexible elongated body. The corresponding square shapes of the keyway and mating key help maintain the rotational orientation of the tool during and after insertion into the channel of the flexible elongated body. However, square-shaped channels may be difficult and expensive to manufacture. Moreover, flexible elongated bodies may be formed of a thin material (e.g., PTFE) that when manipulated into a square shape, may include concentrated stresses in the corners of the resulting shape which may result in defects and/or tears in the flexible elongated body.

In addition to the above, in some medical systems, an imaging probe may be disposed in a flexible elongated device to provide images from inside a patient to ensure the flexible elongated device is navigated to the appropriate procedure site. However, if the imaging probe is misaligned from an expected orientation of the flexible elongated device (e.g., the reference frames of the camera and flexible elongated device are misaligned), this may cause confusion for the operator navigating the flexible elongated device and make it difficult to determine and control the actual position of the flexible elongated body within the patient. Some systems may include a stripe extending within a longitudinal length of an inner surface of a channel of a flexible elongated body to help ensure a desired orientation is provided. Specifically, the imaging probe may image the stripe while the probe is inserted within the flexible elongated body to provide orientation detection of the imaging probe relative to the flexible elongated body. As the imaging probe is moved through the channel, however, the imaging probe may rotate within the flexible elongated body if not constrained. Moreover, orientation detection is reliant upon visibility of the stripe, but the stripe may not extend all the way to a distal end portion of the flexible elongated body and/or saline or other fluids in the flexible elongated body may disguise the stripe. This may result in it being difficult to properly detect the stripe with the imaging probe during use to provide a desired orientation.

In view of the above difficulties, it is desirable to facilitate the insertion of tools into a channel of a flexible elongated device in ways that improve the determination of relative orientations between the tools and the flexible elongate device. In some such embodiments, a flexible elongated device and tool may include mating portions that are configured to rotationally lock the tool relative to the flexible elongated body when the tool is inserted into and engaged with a channel of a flexible elongated body of the flexible elongated device. For example, in some embodiments, the tool may include a mating tool portion disposed along a length of the tool that has a first set of angled flats disposed around an outer cross-sectional perimeter of the mating tool portion. The flexible elongated body of the flexible elongated device may include a mating channel portion disposed along a length of the channel extending through the flexible elongated body. The mating channel portion may include a second set of angled flats disposed around an inner cross-sectional perimeter of the mating channel portion. The mating channel portion may be arranged along a length of the channel of the flexible elongated body such that it mates with the mating tool portion of the tool when the tool is inserted into the channel of the flexible elongated body. In some embodiments, the corresponding angled flats may allow for interlocking of the tool and the flexible elongated body in a finite number of rotational orientations (e.g., at least two). The number of angled flats provided on each of the mating portions may determine the number of possible locked rotational orientations of the medical tool relative to the flexible elongated body.

By providing corresponding angled flats on mating portions of a tool and channel of a flexible elongated body, a flexible elongated device may provide a method for locking the rotational orientation of the tool relative to the flexible elongated body. The tool may be rotationally locked in one of a limited number of possible orientations at any position along a length of the flexible elongated body, even at a distal end portion of the flexible elongated body without the need for a complex shape extending along an extended portion of a channel of a flexible elongated body. Thus, in some embodiments, a channel of the flexible elongated body may be generally circular along a length of the channel that is proximal and/or distal to the mating channel portion depending on its position. A circular working channel is easier and cheaper to produce than square working channels in current medical systems.

The angled shape of the corresponding flats on the mating portions of the tool and the flexible elongated body allow the tool to self-align into one of the limited number of possible orientations. The tool may be inserted into the channel of the flexible elongated in any rotational orientation. As the mating portions of the tool and the flexible elongated body engage, angled shapes of the mating portions may provide a slight rotational torque to rotate the tool relative to the flexible elongated body to automatically lock the tool in one of the limited number of rotational orientations relative to the channel of the flexible elongated body. In addition, the self-aligning nature of the disclosed angled flats on the mating portions may help prevent the tool from catching on the flexible elongated body if the tool is inserted in a misaligned position. As such, a user inserting the tool into the channel does not need to align or rotate the tool relative to the flexible elongated body to achieve locking of the tool within the channel. The tool may automatically lock in one of the limited number of possible rotational orientations. Because there are only a limited number of rotational orientations within the channel, rather than an infinite number of possible rotations, the user may be able to detect which of the limited number of locked orientations the tool is in to synchronize the tool with the flexible elongated body. While these are possible benefits associated with the currently disclosed systems and methods, other benefits may also be possible.

Depending on the embodiment, the types of medical tools used with the various medical systems described herein may include but are not limited to an imaging probe, ablation tool, biopsy needle, electroporation probe, ultrasound probe, and/or any tool where an operator may want to provide and maintain a tool orientation relative to a reference frame of the system. In some embodiments, types of flexible elongated devices that may be used with the described systems and methods may include a catheter, an endoscope, a laparoscope, and/or any other device, including non-medical systems, including a flexible elongated body with a channel that a tool may be inserted through.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical system 100 generally includes a manipulator assembly 102 for operating a medical instrument 104 in performing various procedures on a patient P positioned on a table T. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 106 generally includes one or more control devices for controlling manipulator assembly 102. Manipulator assembly 102 supports medical instrument 104 and may optionally include a plurality of actuators or motors that drive inputs on medical instrument 104 in response to commands from a control system 112. The actuators may optionally include drive systems that when coupled to medical instrument 104 may advance medical instrument 104 into a naturally or surgically created anatomic orifice.

Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may include components of an imaging system (discussed in more detail below), which may include an imaging scope assembly or imaging instrument that records a concurrent or real-time image of a surgical site and provides the image to the operator or operator O through one or more displays of medical system 100, such as one or more displays of display system 110. The concurrent image may be, for example, a two or three-dimensional image captured by an imaging instrument positioned within the surgical site. In some embodiments, the imaging system includes endoscopic imaging instrument components that may be integrally or removably coupled to medical instrument 104. However, in some embodiments, a separate endoscope, attached to a separate manipulator assembly may be used with medical instrument 104 to image the surgical site. In some examples, as described in detail below, the imaging instrument alone or in combination with other components of the medical instrument 104 may include one or more mechanisms for cleaning one or more lenses of the imaging instrument when the one or more lenses become partially and/or fully obscured by fluids and/or other materials encountered by the distal end of the imaging instrument. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 filed Aug. 11, 2016 disclosing "Systems and Methods for Cleaning an Endoscopic Instrument"; U.S. patent application Ser. No. 15/508,923 filed Mar. 5, 2017 disclosing "Devices, Systems, and Methods Using Mating Catheter Tips and Tools"; and U.S. patent application Ser. No. 15/503,589 filed Feb. 13, 2017 disclosing "Systems and Methods for Cleaning an Endoscopic Instrument," each of which is incorporated by reference herein in its entirety. The imaging system may be implemented as hardware, firmware, software or a combination thereof which interact with or are otherwise executed by one or more computer processors, which may include the processors of the control system 112.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

Figures 2A, 2B:
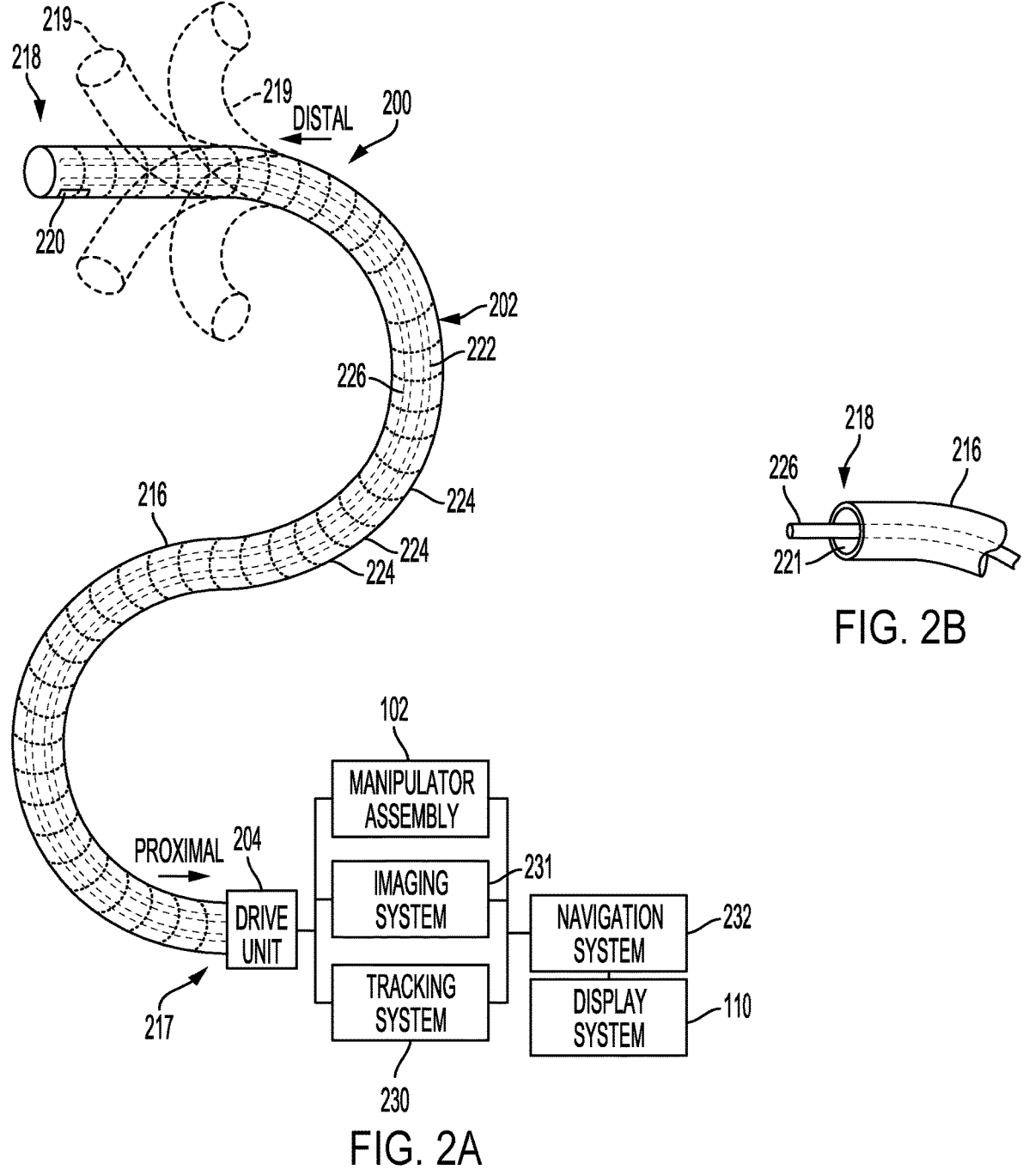
FIG. 2A illustrates a medical instrument system in accordance with some embodiments of the present disclosure.
FIG. 2B illustrates a distal end portion of a medical instrument system in accordance with some embodiments of the present disclosure.

FIG. 2A is a simplified diagram of a medical instrument system 200 according to some embodiments. Medical instrument system 200 includes a flexible elongated device 202, such as a flexible catheter, coupled to a drive unit 204. Flexible elongated device 202 includes a flexible elongated body 216 having proximal end 217 and distal end or tip portion 218. Medical instrument system 200 further includes a tracking system 230 for determining the position, orientation, speed, velocity, pose, and/or shape of distal end 218 and/or of one or more segments 224 along flexible elongated body 216 using one or more sensors and/or imaging devices as described in further detail below.

Tracking system 230 may optionally track distal end 218 and/or one or more of the segments 224 using a shape sensor 222. Shape sensor 222 may optionally include an optical fiber aligned with flexible elongated body 216 (e.g., provided within an interior channel (not shown) or mounted externally). The optical fiber of shape sensor 222 forms a fiber optic bend sensor for determining the shape of flexible elongated body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongated device may be determined using other techniques. For example, a history of the distal end pose of flexible elongated body 216 can be used to reconstruct the shape of flexible elongated body 216 over the interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

Flexible elongated body 216 includes a channel 221 sized and shaped to receive a medical instrument 226, which may also be referred to as a tool herein. FIG. 2B is a simplified diagram of flexible elongated body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible elongated body 216 and used at a target location within the anatomy. Medical instrument 226 may include, for example, image capture probes, biopsy instruments, laser ablation fibers, and/or other surgical, diagnostic, or therapeutic tools. Medical instrument 226 may be used with an imaging instrument (e.g., an image capture probe) also within flexible elongated body 216. The imaging instrument may include a cable coupled to the camera for transmitting the captured image data. In some examples, the imaging instrument may be a fiber-optic bundle, such as a fiberscope, that couples to image processing system 231. The imaging instrument may be single or multi-spectral, for example capturing image data in one or more of the visible, infrared, and/or ultraviolet spectrums. Medical instrument 226 may be advanced from the opening of channel 221 to perform the procedure and then retracted back into the channel when the procedure is complete. Medical instrument 226 may be removed from proximal end 217 of flexible elongated body 216 or from another optional instrument port (not shown) along flexible elongated body 216.

Flexible elongated body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongated devices are described in detail in U.S. patent application Ser. No. 13/274,208 (filed Oct. 14, 2011) (disclosing "Catheter with Removable Vision Probe"), which is incorporated by reference herein in its entirety.

The information from tracking system 230 may be sent to a navigation system 232 where it is combined with information from image processing system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3:
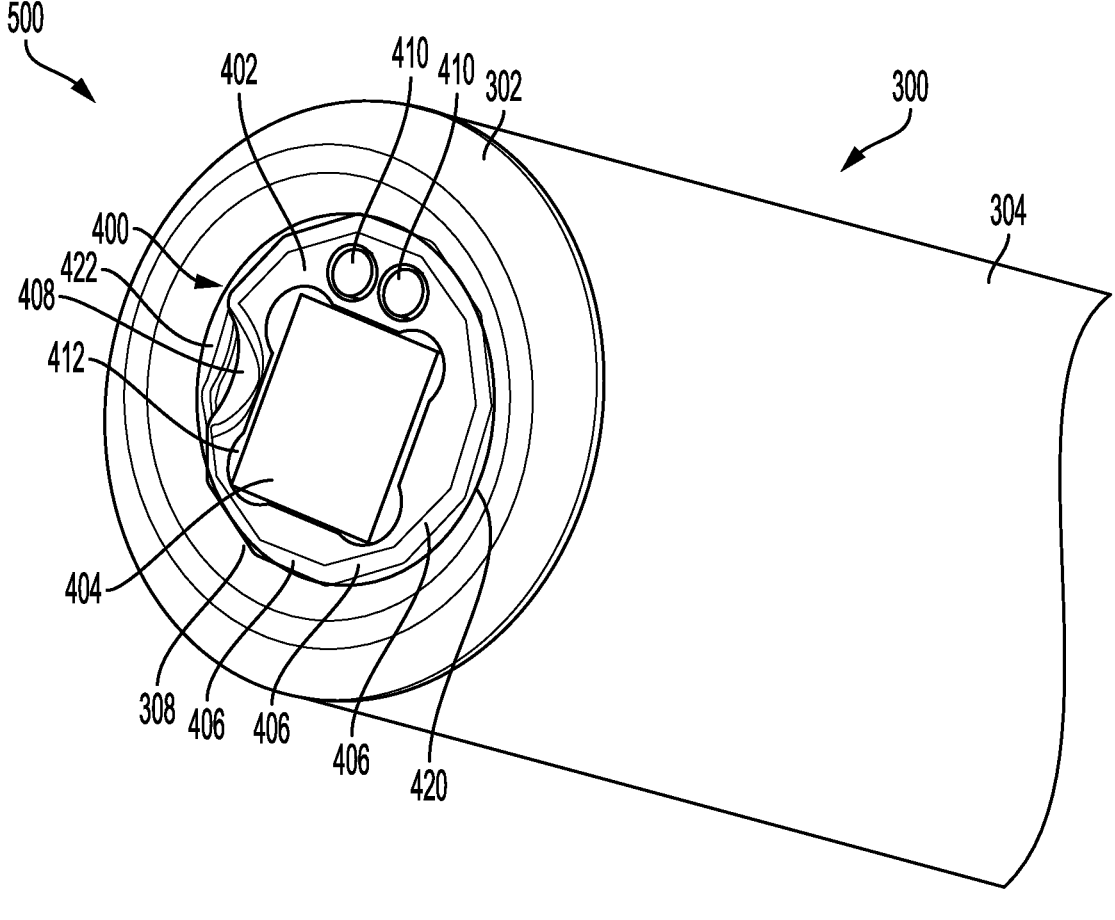
FIG. 3 illustrates a flexible elongated device including a tool disposed in a channel of the flexible elongated device, in accordance with some embodiments of the present disclosure.

FIG. 3 shows an embodiment of a medical instrument 500 including a tool 400 disposed within a channel 308 of a flexible elongated body 300. In some embodiments, the flexible elongated body 300 may be part of a flexible elongated device as described above with respect to FIG. 2. The flexible elongated body 300 may include a mating channel portion 302 that is configured to be engaged with a corresponding mating tool portion 402 of the tool 400 to maintain a rotational orientation of the tool 400 with respect to the flexible elongated body 300. For example, the tool 400 may include the mating tool portion 402 that mates with the mating channel portion 302 and rotationally lock the tool 400 relative to the flexible elongated body 300. In the depicted embodiment, the mating channel portion 302 is a separately formed component that is attached to a shaft 304 of the flexible elongated body, though embodiments in which an integrally formed mating channel portion is used are also contemplated. The mating channel portion 302 is located at a distal end portion of the flexible elongated body 300. In other examples, the mating channel portion 302 may be disposed at any desired location along a length of the shaft 304 of the flexible elongated body 300, such as at a more proximal location along the shaft 304. The mating tool portion 402 may be located at a corresponding axially aligned location when the tool 400 is fully inserted into the channel 308 of the flexible elongated body 300. In the depicted embodiment, the mating tool portion 402 may be disposed at a distal end portion of the tool 400. However, in other embodiments, the mating channel portion 302 may disposed at a portion of the channel 308 that is proximal to an articulatable portion (e.g., distal end 218) of the flexible elongated body 300.

While the tool 400 may be any type of tool, in one example, the tool 400 is an imaging probe that includes an imaging device 404 disposed within an aperture 412 of the tool 400. As shown in FIG. 3, the imaging device 404 and the aperture 412 of the tool 400 may have complimentary cross-sectional shapes that are approximately square, or any other appropriate shape, to fix the imaging device 404 to the tool 400. As shown in FIG. 3, in some embodiments, the aperture 412 may include rounded corners. The tool 400 may also include one or more illumination fibers 410 which may be disposed in one or more corresponding openings extending formed in a distal end portion of the tool. The illumination fibers may be used to provide illumination to the surrounding environment.

To rotationally lock the tool 400 relative to the flexible elongated body 300, in some embodiments, the mating tool portion 402 may include two or more angled flats 406 disposed around a cross sectional perimeter of the mating tool portion 402. As shown in FIG. 3, the angled flats 406 may be disposed around a transverse cross sectional perimeter at a distal end of the mating tool portion 402. The angled flats 406 may engage corresponding angled flats 306 (see FIGS. 4-5) on the mating channel portion 302 of the flexible elongated body 300. As shown in FIG. 3, the mating tool portion 402 and mating channel portion 302 are located at a distal end portion of the tool 400 and elongated body 300, respectively. However, the mating tool portion 402 and the mating channel portion 302 may be positioned at any distance along the flexible elongated body 300. Possible dimensions for these mating portions of the tool 400 and channel of the flexible elongated body 300 are elaborated on further below.

Figure 4:
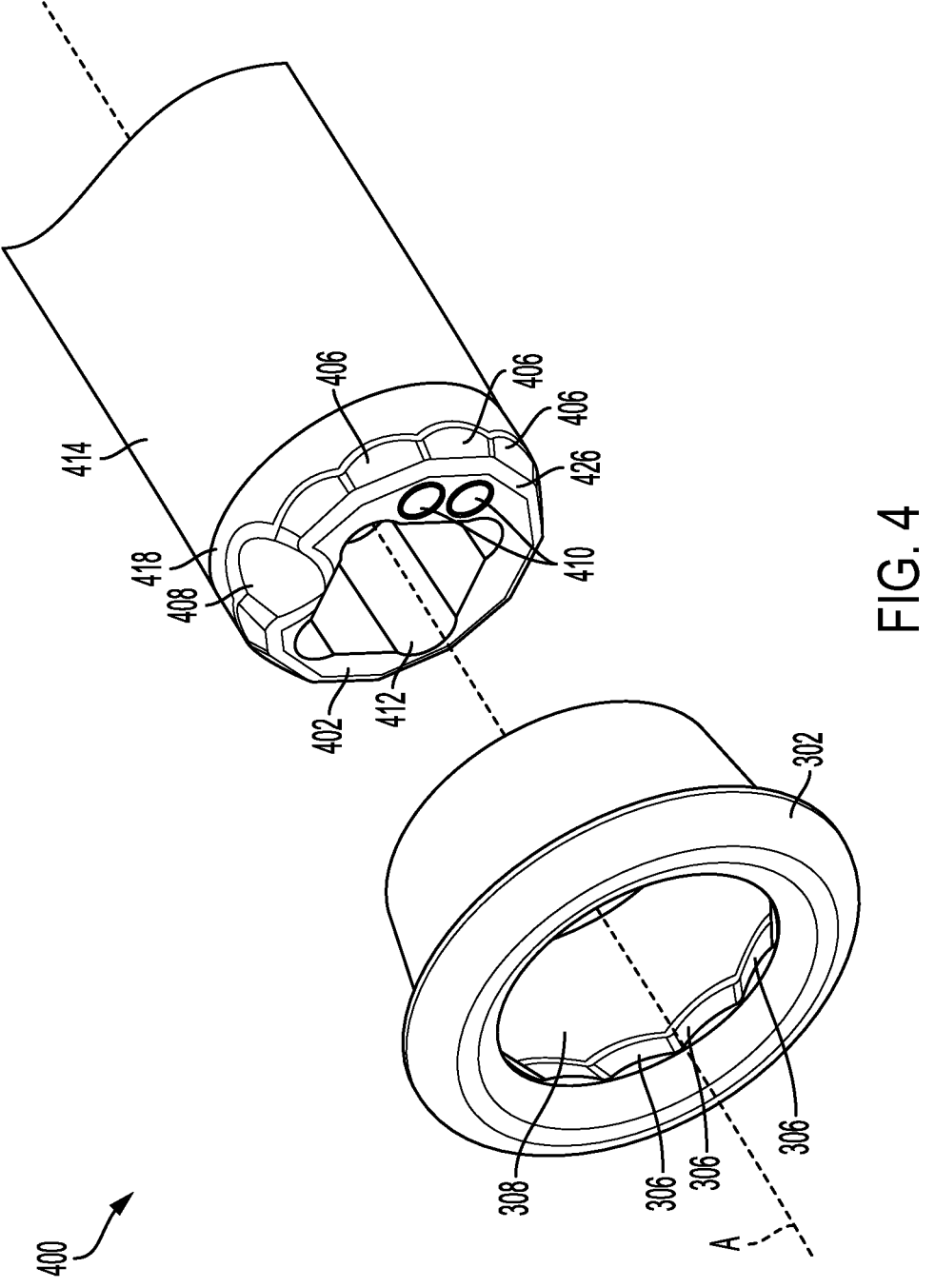
FIG. 4 illustrates mating portions of the tool and channel of the flexible elongated device shown in FIG. 3 in accordance with some embodiments of the present disclosure.

The flats 406 of the tool 400 may be located on an exterior surface of the tool 400 and the flats 306 of the mating channel portion 302 may be located on an interior surface of the channel 308 of the flexible elongated body 300. As best shown in FIG. 4, the mating tool portion 402 and mating channel portion 302 may each include a corresponding number of angled flats 306 and 406 that are arranged in a pattern around the perimeter and configured to be engaged with each other. The flats 306 and 406 may have corresponding structures that facilitate rotational locking. For example, the flats 306 and 406 may have the same shape, width, and/or spacing such that the flats 306 and 406 that face each other may be pressed against each other when the mating tool portion 402 and mating channel portion 302 are engaged with one another during tool insertion through the channel 308 of the flexible elongated body 300. In some embodiments, the angled flats 406 of the tool 400 and the angled flats 306 of the flexible elongated body 300, when engaged, mate with each other to form a sealed surface 420 between the tool 400 and the flexible elongated body 300, see FIG. 3 and FIGS. 6-7.

Referring again to FIGS. 3-4, the number of angled flats 306 and 406 determines the number of rotational positions in which the tool 400 may lock relative to the flexible elongated body 300. Thus, in some embodiments, the channel and tool mating portions 302 and 402 may include 4 to 12 corresponding angled flats. In some embodiments, the mating portions may include 6 to 8 angled flats. However, any appropriate number of flats may be used. The flats arranged around a perimeter of the mating channel portion 302 and mating tool portion may have either similar or different widths around the perimeter and may be uniformly or non-uniformly distributed around the perimeter. In a non-limited example, a mating tool portion and mating channel portion may have a circular cross section with 4 spaced apart angled flats provided in opposite corners around the perimeter of the cross section.

As shown in FIG. 3, the tool 400 may also include a divot 408 disposed on the external perimeter of the tool mating portion 402. The divot may extend radially inward. The divot 408 may be arranged between adjacent angled flats 406. The divot 408 may have various widths. In one example, the divot 408 has the width of an angled flat 406. In another example, the divot 408 may have a width that is greater than a width of an angled flat 406 such that the divot 408 extends into a region of the two adjacent flats 406. However, embodiments, in which the divot 408 has a width that is smaller than a corresponding width of the angled flats 406 are also contemplated. The divot 408 provides a fluid channel 422 extending through the sealed surface 420 formed between the corresponding flats 306, 406 of the flexible elongated body 300 and tool 400, see FIGS. 6 and 7. As elaborated on below, the fluid channel 422 may be in fluid communication with a liquid reservoir that is proximal to the flexible elongated body 300 such that saline or other appropriate fluid may be dispensed through the flexible elongated body 300 and fluid channel 422 formed in the sealed surface 420. In some embodiments, the saline, or other appropriate fluid, may be passed through the fluid channel 422 to clean the imaging device 404 or any other component of the tool 400 disposed on the flexible elongated body 300.

FIG. 4 shows a schematic of a tool 400 adjacent to a mating channel portion 302 of a flexible elongated body 300 prior to engagement according to some embodiments. Specifically, the tool 400 may include a mating tool portion 402 disposed at a desired position along a length of the tool 400, and in the depicted embodiment, at a distal end portion of the tool 400. In some embodiments, the tool 400 may include a sleeve 414 that is attached to and extends proximally from the mating tool portion 402. To show the desired relationships, the shaft 304 of the flexible elongated body 300 (see FIG. 3) has been omitted from FIG. 4 to illustrate the features of the tool 400 and the mating tool portion 402.

The mating tool portion 402 may include a distal end portion 418 with the angled flats 406 disposed uniformly around an outer perimeter of the distal end portion 418 of the mating tool portion 402. In some embodiments, the angled flats may form a truncated pyramid shape on the distal end portion 418 of the mating tool portion 402. Similarly, the mating channel portion 302 of the flexible elongated body 300 includes angled flats 306 disposed around an inner perimeter of the channel 308 extending through the mating channel portion 302 to form a correspondingly sized and shaped cavity to receive the truncated pyramid, or other shape, of the mating tool portion 402. The angled flats 306 and 406 of the mating channel portion 302 and mating tool portion 402 may be angled relative to a longitudinal axis A extending through the flexible elongated body 300, and tool 400 when disposed therein, such that the angled flats extend in a distal direction with the radial position decreasing in a distal direction along the angled flats. Due to the complementary shape and orientation of the angled flats 306 and 406, the angled flats 306 of the tool may be abutted against surfaces of flats 406 of the tool 400 when the tool 400 is inserted into and engaged with the flexible elongated body 300.

Figure 5:
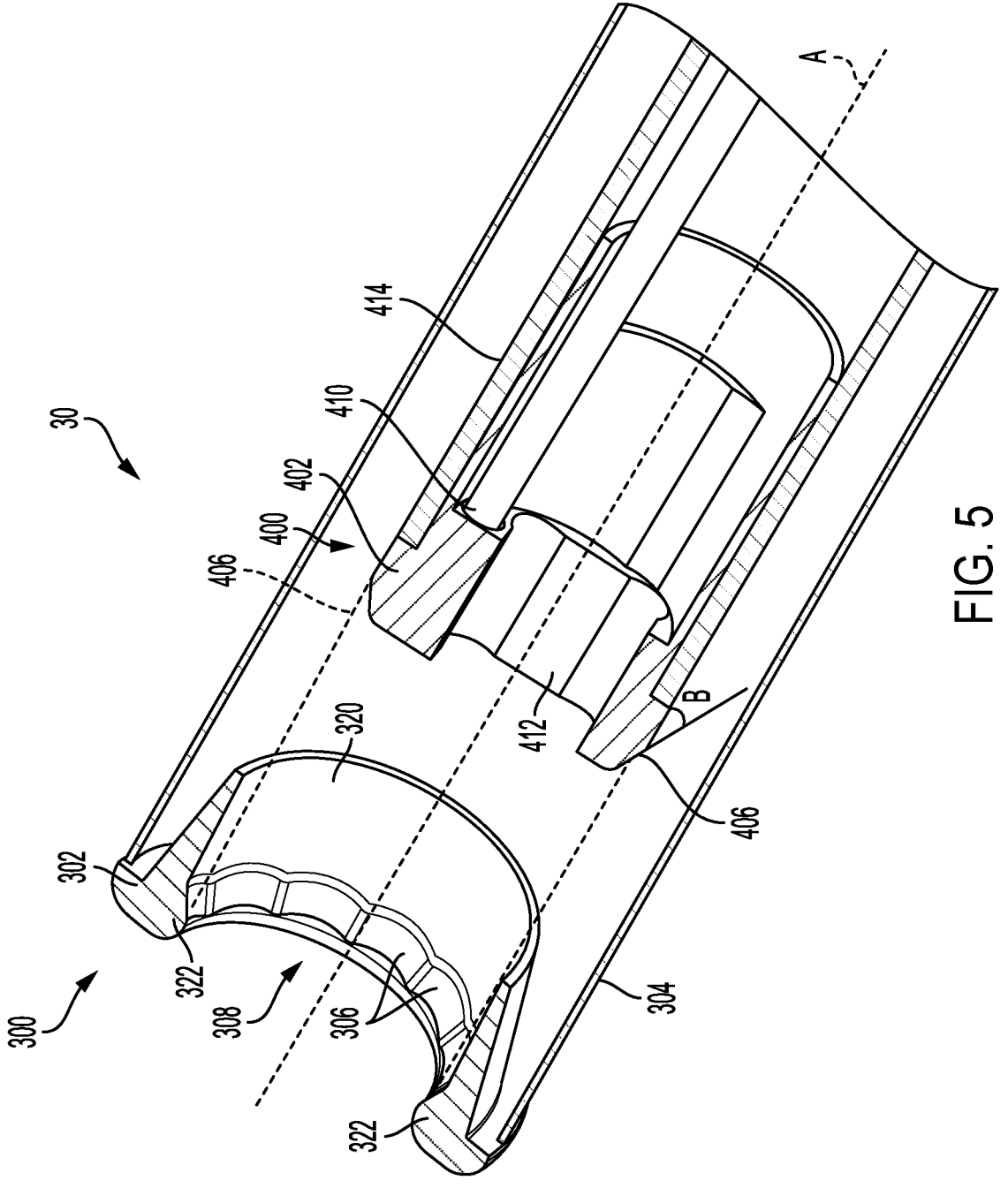
FIG. 5 illustrates a cross-sectional view of the flexible elongated device of FIG. 3 as the tool advances toward a distal portion of the flexible elongated device including a corresponding mating channel portion in accordance with some embodiments of the present disclosure.

As best seen in FIGS. 4 and 5, in some embodiments, a maximum outer transverse dimension, such as an outer diameter, of a mating tool portion 402 as disclosed in the embodiments described herein may be selected for insertion into a channel of a flexible elongated body. Thus, a maximum outer transvers dimension of a mating tool portion may be between or equal to approximately 1 mm and 20 mm. A channel of a flexible elongated body that the tool is inserted into may exhibit a corresponding transverse dimension (e.g., diameter). A length of the mating tool portion 402 may also be between or equal to about 10 mm and 30 mm. In some embodiments, a length of the flats 406 in a direction oriented parallel to a longitudinal axis A of the tool 400 may be between or equal to approximately 0.5 mm and 5 mm. While specific ranges for dimensions of the various components are described above, it should be understood that other dimensions both greater and less than those noted above are also contemplated.

In some embodiments, the angled flats 306, 406 of the mating tool portion 402 and the mating channel portion 302 provide several manufacturing advantages. For example, the mating tool portion 402 and mating channel portion 302 are relatively small components which may be challenging to manufacture. As shown in FIG. 4, the angled flats 406 may be positioned on an outer distal end portion of the mating tool portion 402. This outer position and flat shape may allow the flats to be easily milled onto a desired portion of a tool 400 despite the small size of the mating tool portion 402. Similarly, including flats 306 on an inner channel 308 of a flexible elongated body 300 may be more difficult to mill and may require a tool that extends into the channel. Such tools may break during milling and/or damage the flexible elongated body. In contrast, the angled flats 306 formed on an insert or other component that is attachable to the flexible elongated body 300 may be relatively easier to manufacture. Depending on the embodiment, the mating channel portion and the mating tool portion may be produced using any appropriate manufacturing method including, but not limited to plastic injection molding, metal injection molding (MIM), additive manufacturing, machining, molding, micro-electromechanical machines (MEMs) manufacturing techniques, and/or any other appropriate method. These mating components may be formed of any appropriate material including metal, plastic, and/or ceramic.

In some embodiments, as the tool 400 approaches the mating channel portion 302, the angled flats 306 and 406 of the flexible elongated body 300 and tool 400 may cause the mating tool portion 402 to rotate to align and lock with the mating channel portion 302 in a limited number of rotational orientations. The embodiment shown in FIG. 4, for example, includes 12 corresponding angled flats, and therefore the tool 400 may rotationally lock relative to the flexible elongated body in 12 different positions. Other numbers of interlocking angled flats may also be used. For example, fewer angled flats (e.g., 2 flats) provides fewer possible rotational orientations of the tool within the channel, and thus can facilitate the accuracy of rotational orientation determination using various types of sensors. However, when there are fewer flats, self-alignment may be more difficult and a user may need to rotate the tool within the channel to achieve a locking position. A larger number of angled flats may facilitate self-alignment of the mating portions and cause the tool to automatically twist into one of the possible limited rotational locking positions, but may reduce the accuracy of rotational orientation determination using a sensor because there are more possible locking positions that are separated by smaller rotational angles.

The angled flats 306 and 406 may also provide self-aligning of the tool 400 relative to the flexible elongated body 300. In some embodiments, the mating tool portion 402, may have an axial load applied to it as it is inserted into an aperture 412 and mates with the mating channel portion 302 of the flexible elongated body 300. In instances where the mating tool portion 402 and mating channel portion 302 are misaligned during this initial insertion, the tool 400, and mating tool portion 402 may twist into a proper locking position under the applied distally directed axial load because of the shapes of the flats 306 and 406 (e.g., and without rotational force being applied to the tool by an operator or programmatically, such as by controller system 112). For example, the flats 406 on the mating tool portion 402 may not be aligned rotationally with the flats 306 on the mating channel portion 302 during insertion. As such, the tool 400 may need to rotate slightly to lock into one of the possible rotational orientations. The shape of the flats may provide a slight rotational torque when the mating tool portion is pressed against the mating channel portion of the flexible elongated body. As such, the self-aligning capability provided by the flats for locking in a position can be relied upon and there is no need to monitor or control the rotational orientation of the tool 402 during insertion. A fewer number of flats may require a larger rotation, and correspondingly larger force, to rotate into the locked position. Regardless of the rotational orientation of the mating tool portion 402 as the tool 400 approaches the mating channel portion 302, the angled flats 306 of the mating channel portion 302 may apply a rotational torque to the corresponding angled flats 406 of the tool 400 to cause the tool 400 to twist into a proper rotational position as the mating tool portion 402 is inserted and mated with the mating channel portion 302. This self-aligning behavior is elaborated on further below.

As noted above, in some embodiments, the complimentary angled arrangement of the angled flats 306 and 406 of the mating channel portion 302 and mating tool portion 402 may enable self-alignment of the tool 400 within the flexible elongated body 300 during insertion of the tool 400. For example, the mating tool portion 402 may be displaced in a distal direction towards the mating channel portion 302 in a rotational orientation that is misaligned with one of the possible locked rotational orientations (i.e., the angled flats 406 on the tool 400 may not be aligned with the angled flats 306 on the flexible elongated body 300). As such, a leading edge or corner of the various angled flats 406 of the tool 400 may be pressed against the surfaces of the corresponding angled flats 306 of the mating channel portion 402. This contact during distal motion of the tool 400 applies a rotational torque 400 to the tool that causes the tool to rotate towards the nearest aligned orientation where the angled flats 306 and 406 of the mating channel portion 302 and mating tool portion 402 may be engaged with one another. Thus, the disclosed methods and systems may promote the self-alignment and locking of a tool 400 into one of a plurality of permitted orientations during insertion.

In embodiments in which an imaging device 404 is disposed within an aperture 412 of the mating tool portion 402 (see FIG. 3), the alignment and locking of the tool 400 relative to the flexible elongated body 300 described above may allow the imaging device 404 to be rotationally locked within the flexible elongated body 300 in a limited number of orientations. For example, in the embodiment shown in FIG. 3, because the mating tool portion 402 includes 12 angled flats 406, the imaging device 404 may be locked in one of 12 rotational orientations within the flexible elongated body 300.

In some embodiments, once the imaging device 404 is rotationally locked within the flexible elongated body 300, the rotational orientation of the imaging device 404, or other tool 400, relative to the flexible elongated body may be determined. In a non-limited example, real time images captured from the imaging device 404 may be compared to virtual images that simulate what the imaging device 404 should be capturing in view of its position and orientation. The virtual images may be images of an anatomy, such as an anatomical passageway where the flexible elongated device 202 is located. The virtual images may be generated based on a three-dimensional model created from a computed tomography (CT) scan of the anatomy. The control system 112 may compare the real images to the virtual images to determine the rotational orientation of the tool 400 within the flexible elongated body 300. The determined rotational orientation using the image comparison may then be best fit to one of the limited number of possible positions of locking for the angled flats 306 and 406. The limited number of possible locking positions provides for greater accuracy for rotational orientation determination.

Other appropriate methods for determining an orientation of the tool 400 within the flexible elongated body 300 may be used including but not limited to sensors, visual marker identification, and/or any other appropriate method. Whichever method is used, the determined rotational orientation may be best fit to one of the limited number of possible positions of locking for the angled flats 306 and 406.

In addition, because the angled flats maintain the rotational orientation of the tool 400 and the flexible elongated body 300, the rotational orientation of the tool only needs to be determined once during a procedure or once each time a tool is inserted.

As shown in FIG. 4, in some embodiments, it may be desirable to avoid the inclusion of sharp edges and corners on a tool 400 inserted into a flexible elongated body. Accordingly, the angled flats 406 on a mating tool portion 402 of a tool 300 may each include rounded edges and/or corners. This is illustrated by the inclusion of a fillet, chamfer, or other appropriately rounded edge 426 located on the distal end portion of the angled flats 406. These rounded edges 426 may also be disposed between adjacent angled flats as well. The inclusion of rounded edges and/or corners may provide smooth surfaces and transitions that may help to prevent the tool 400 from catching on and damaging an inner surface of a channel 308, internal sleeve disposed in the channel (not depicted), or other portion of the flexible elongated body 300 during tool insertion.

Figure 6:
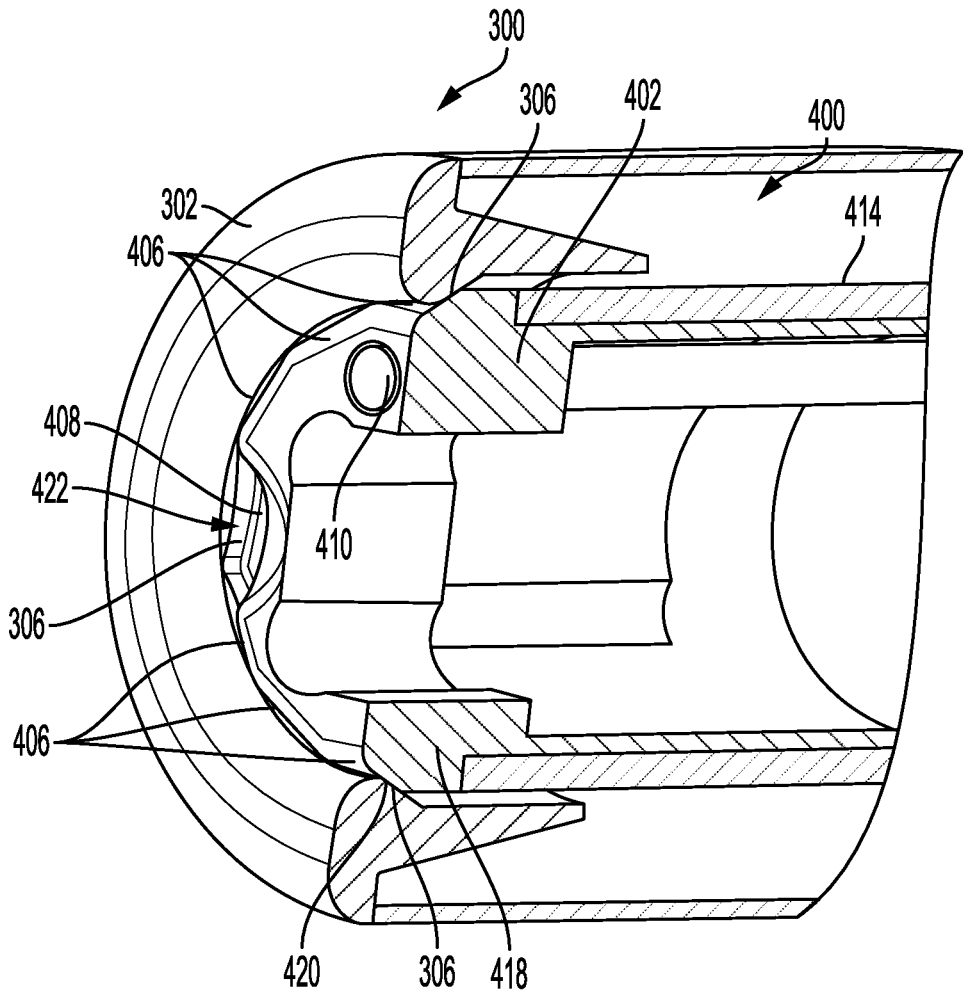
FIG. 6 illustrates a cross-section view of the flexible elongated device of FIG. 3 with the tool disposed in a distal portion of the flexible elongated device such that it is engaged with a mating channel portion in accordance with some embodiments of the present disclosure.

FIG. 5 shows a cross-sectional view of the mating tool portion 402 of a tool 400 being displaced distally towards a mating channel portion 302 within a channel 308 of the flexible elongated body 300 and FIG. 6 shows a cross-sectional view of the mating tool portion 402 engaged with the mating channel portion 302. In some embodiments, each of the angled flats 406 are angled relative to a longitudinal axis A of the flexible elongated body 300 when the tool is inserted into a channel 308 of the flexible elongated body. The corresponding angled flats 306 of the mating channel portion 302 may have complementary angles relative to the angled flats 406 of the mating tool portion. Accordingly, the corresponding flats 306, 406, as shown in FIG. 6, have surfaces that abut each other to form a sealed surface 420 when the tool 400 and the flexible elongated body 300 are in an engaged position with an interface extending between these surfaces also being angled relative to the longitudinal axes of the flexible elongated body 300 and/or the tool 400.

As shown in FIG. 5, in some embodiments, the angled flats 406 may be oriented at an angle B relative to a longitudinal axis A of the flexible elongated body 300 and/or tool 400. For example, the angle B may be between or equal to approximately 10 degrees and 50 degrees, or more preferably between or equal to approximately 10 degrees and 40 degrees. In some embodiments, angle B may be between or equal to approximately 20 degrees and 30 degrees, including, for example, approximately 25 degrees. The angle of the angled flats 306 of the mating channel portion 302 may form complementary angles to those noted above relative to tool 400. Thus, the angled flats 306 may be oriented at angles relative to the longitudinal axis of the flexible elongated body that are also within the above noted ranged. The angle B may be selected to provide a sufficiently sized surface area of each flat 406 to engage surfaces of corresponding flats 306 of the mating channel portion and provide self-aligning capabilities. As described above, the angled flats provide a rotational torque to the tool 400 when the mating tool portion 402 is pressed against the mating channel portion 302 of the flexible elongated body 300. The angle of the flats may determine the amount of torque, and corresponding applied axial force, needed to rotate the tool. An angle that is too small may not provide sufficient surface area to allow the flats to self-align. On the other hand, an angle that is too large may result in the distal end portion 418 of the mating tool portion 402 extending too far in a longitudinal direction, making the mating tool portion larger than may be desirable for medical uses in elongated bodies.

As shown in FIG. 5, the angled flats 306 of the mating channel portion 302 of the flexible elongated body extend radially inward from an inner channel wall 320 into the channel 308. The 306 flats extend further into the channel 308 in a distal direction, forming a tapered inner radius 322 that is smaller at a distal end portion of the mating channel portion 302 relative to a proximal portion of the mating channel portion 302. To avoid a tool from snagging during extension and/or use after insertion, it may be desirable to include a tapered inner radius 322 formed by the flats 306 on a mating channel portion 302. This may provide a curved surface to prevent a portion of a tool 400 (such as an extending biopsy needle or other structure) from catching on the mating channel portion 302 during operation.

Figure 7:
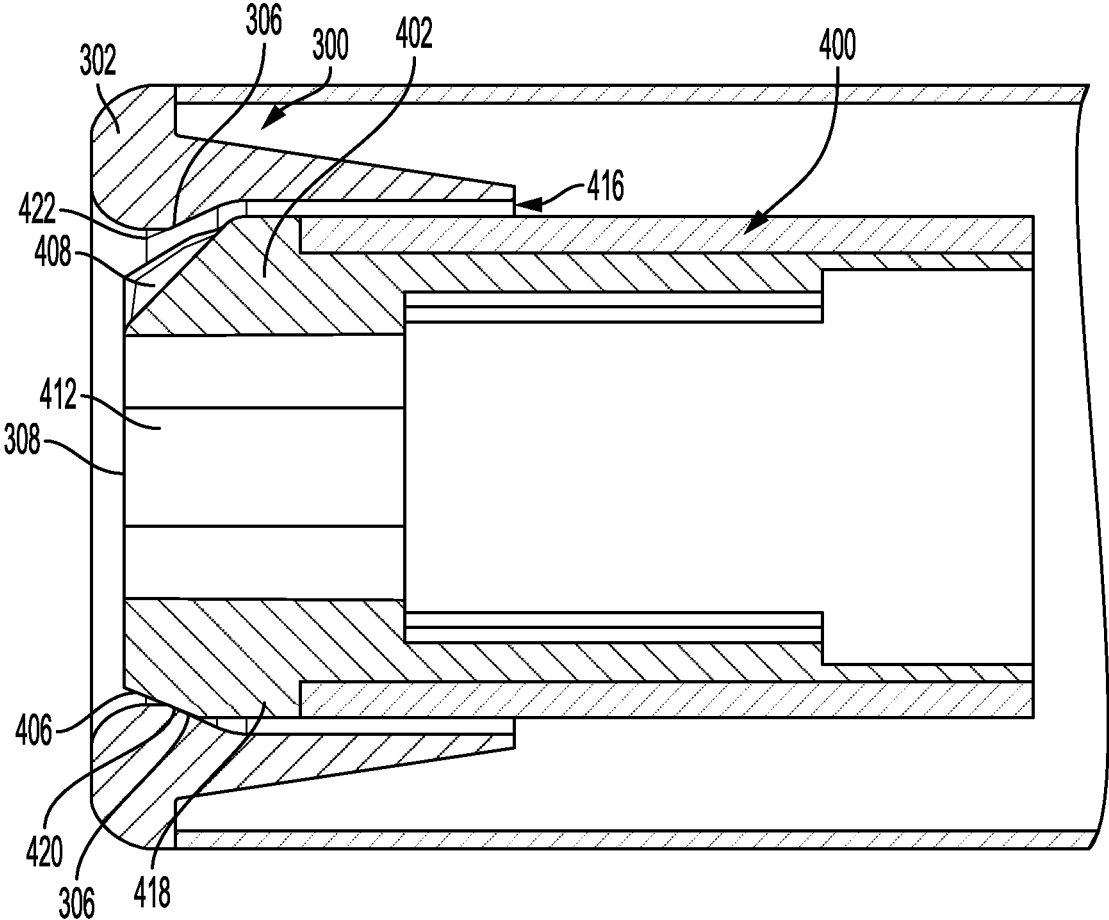
FIG. 7 illustrates a cross-section view of the flexible elongated device of FIG. 3 with the tool disposed in a distal portion of the flexible elongated device such that it is engaged with a mating channel portion in accordance with some embodiments of the present disclosure.

FIG. 7 shows a cross-sectional view of a mating tool portion 402 of a tool 400 engaged with a mating channel portion 302 of a flexible elongated body 300, taken through a divot 408 formed on a perimeter of a distal end portion of the mating tool portion 402. As shown in FIG. 7, the angled flats 406 of the mating tool portion 402 form a sealed surface 420 with the angled flats 306 of the mating channel portion 302 when the angled flats are engaged with one another. The sealed surface 420 may extend at least partially around the perimeter of the engaged mating tool portion 402 and mating channel portion 302. In some embodiments, the divot 408 may extend radially inwards into a distal end portion 418 of the mating tool portion 402 to provide a fluid channel 422 disposed between the mating tool portion 402 and the mating channel portion 302 and extending from a proximal side of the sealed surface 420 to a distal side of the sealed surface 420. As shown in FIG. 7, fluid (e.g., saline or other liquid or a gas) may flow through a channel 416 formed between the mating tool portion and the mating channel portion from a fluidly coupled liquid reservoir, not depicted, and through the fluid channel 422 provided by the divot 408. The sealed surface 420 may help direct the fluid through the divot 408. In some embodiments, the fluid may be used to clean a lens of an imaging device 404 of the tool 400.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

The invention claimed is:

1. A medical instrument comprising:
   a tool including a mating tool portion disposed on a distal portion of the tool, the mating tool portion with a first set of angled flats disposed around a cross sectional perimeter of the mating tool portion; and
   a flexible elongated body including a channel extending through the flexible elongated body, wherein the tool is insertable into the channel, and wherein the channel includes a mating channel portion disposed on a distal portion of the channel, the mating channel portion with a second set of angled flats disposed around a cross sectional perimeter of the mating channel portion;
   wherein the first set of angled flats of the mating tool portion and the second set of angled flats of the mating channel portion are angled relative to a longitudinal axis of the flexible elongated body when the tool is inserted in the channel, and wherein the first set of angled flats of the mating tool portion engages with the second set of angled flats of the mating channel portion in one of a plurality of possible rotational orientations when the tool is inserted into the channel.

2. The medical instrument of claim 1, wherein the first set of angled flats and the second set of angled flats maintain a rotational orientation of the tool within the channel of the elongated flexible elongated body.

3. The medical instrument of claim 1, wherein the first set of angled flats and the second set of angled flats causes the mating tool portion to twist into one of the plurality of possible rotational orientations when a distally directed force is applied to the tool during insertion.

4. The medical instrument of claim 1, wherein the mating channel portion is disposed on a portion of the channel proximal to an articulatable portion of the flexible elongated body.

5. The medical instrument of claim 1, wherein the first set of flats is disposed on an outer surface of the tool and the second set of flats is disposed on an inner surface of the channel.

6. The medical instrument of claim 1, wherein the tool and the flexible elongated body each include between or equal to 4 and 12 angled flats.

7. The medical instrument of claim 1, wherein the angled flats are arranged at an angle between 10 degrees and 40 degrees relative to the longitudinal axis of the flexible elongated body when the tool is inserted into the channel.

8. The medical instrument of claim 1, wherein the angled flats of the tool and the flexible elongated body form a seal when mated together.

9. The medical instrument of claim 8, wherein the mating tool portion of the tool includes a divot configured to provide a fluid channel through the seal when the angled flats are mated together.

10. The medical instrument of claim 1, wherein the channel has a circular cross-sectional shape proximal to the mating channel portion.

11. The medical instrument of claim 1, wherein one of the first set of angled flats and the second set of angled flats form a truncated pyramid and the other of the first set of angled flats and the second set of angled flats is sized and shaped to receive the truncated pyramid.

12. A method for inserting a tool into a medical instrument, the method comprising:
   advancing the tool through a channel extending through a flexible elongated body of the medical instrument; and
   engaging a first set of angled flats of a mating tool portion of the tool disposed on a distal portion of the tool with a second set of angled flats of a mating channel portion of the channel disposed on a distal portion of the channel in one of a plurality of possible rotational orientations, wherein the first set of angled flats and the second set of angled flats are angled relative to a longitudinal axis of the channel when the tool is disposed in the channel.

13. The method of claim 12, further comprising maintaining a rotational orientation of the tool within the channel of the elongated flexible elongated body with the first set of angled flats and the second set of angled flats.

14. The method of claim 12, further comprising applying a distally directed force to the tool during insertion to cause the mating tool portion to twist into one of the plurality of possible rotational orientations due to the first set of angled flats and the second set of angled flats.

15. The method of claim 12, wherein the mating channel portion is disposed on a portion of the channel proximal to an articulatable portion of the flexible elongated body.

16. The method of claim 12, wherein the first set of flats are disposed on an outer surface of the tool and the second set of flats is disposed on an inner surface of the channel.

17. The method of claim 12, further comprising forming a seal between the angled flats of the tool and the flexible elongated body.

18. The method of claim 17, further comprising forming a fluid channel through the seal via a divot in the mating tool portion of the tool when the angled flats are mated together.

* * * * *